(12) United States Patent
Niimi (10) Patent No.: US 11,644,445 B2
(45) Date of Patent: May 9, 2023

(54) METHOD FOR EVALUATING CORRODED PART

(71) Applicant: Kunihiko Niimi, Aichi (JP)

(72) Inventor: Kunihiko Niimi, Aichi (JP)

(73) Assignee: KUNIHIKO NIIMI, Aichi (JP)

( * ) Notice: Subject to any disclaimer, the term of this patent is extended or adjusted under 35 U.S.C. 154(b) by 0 days.

(21) Appl. No.: 17/189,958

(22) Filed: Mar. 2, 2021

(65) Prior Publication Data

US 2021/0181155 A1     Jun. 17, 2021

Related U.S. Application Data

(63) Continuation of application No. PCT/JP2018/032636, filed on Sep. 3, 2018.

(51) Int. Cl.
| | | |
|---|---|---|
| *G01N 29/11* | (2006.01) | |
| *G01N 33/2045* | (2019.01) | |
| *G01N 29/265* | (2006.01) | |
| *G01N 29/44* | (2006.01) | |
| *G01N 29/24* | (2006.01) | |

(52) U.S. Cl.
CPC ............. *G01N 29/11* (2013.01); *G01N 29/24* (2013.01); *G01N 29/265* (2013.01); *G01N 29/44* (2013.01); *G01N 33/2045* (2019.01); *G01N 2291/028* (2013.01); *G01N 2291/0234* (2013.01); *G01N 2291/048* (2013.01); *G01N 2291/102* (2013.01)

(58) Field of Classification Search
CPC ........ G01N 29/11; G01N 29/24; G01N 29/44; G01N 2291/0234; G01N 2291/028; G01N 2291/048; G01N 2291/102; G01N 29/265; G01N 33/2045

USPC .......................................................... 73/600
See application file for complete search history.

(56) References Cited

U.S. PATENT DOCUMENTS 10,295,435 B1 * 5/2019 Wu .................... G01M 7/02

FOREIGN PATENT DOCUMENTS

| CA | 2677893 A1 * | 8/2008 | ............. G01B 17/08 |
|---|---|---|---|
| JP | 2004077234 A * | 3/2004 | |
| JP | 2004-361321 A | 12/2004 | |

(Continued)

OTHER PUBLICATIONS

International Search Report issued in realted parent International Patent Application No. PCT/JP2018/032636, dated Nov. 20, 2018, with English translation.

*Primary Examiner* — Lisa M Caputo
*Assistant Examiner* — Rose M Miller
(74) *Attorney, Agent, or Firm* — McDermott Will & Emery LLP (57) ABSTRACT

To provide a method for evaluating a corroded part, the method making it possible to specify only a waveform reflected by a corroded part and to evaluate the waveform. When a transmission unit (2) is moved on the surface of a metal pipe (60) and the distance between a corroded part (5) and the transmission unit (2) is changed, only a waveform portion A of ultrasonic waves reflected by the corroded part (5) moves toward the left or right along an X axis, and only the intensity of a noise waveform portion B included in a received wave changes upward or downward along a Y axis, which makes it possible to separate the waveform portion A and the noise waveform portion B of a longitudinal-wave surface wave reflected by the corroded part (5) and evaluate the waveform portion A in detail.

2 Claims, 7 Drawing Sheets

(56) References Cited

FOREIGN PATENT DOCUMENTS

| JP | 3705357 | B2 | * | 10/2005 | | |
|---|---|---|---|---|---|---|
| JP | 3198840 | U | | 7/2015 | | |
| JP | 6124191 | B1 | * | 5/2017 | | |
| JP | 2018028509 | A | * | 2/2018 | ............ | G01B 17/08 |
| JP | 6385017 | B1 | * | 9/2018 | | |

* cited by examiner

METHOD FOR EVALUATING CORRODED PART

RELATED APPLICATION

This application is a Continuation Application of International Application No. PCT/JP2018/32636, filed on Sep. 3, 2018. The subject matter is incorporated herein by reference in entirety.

TECHNICAL FIELD

The present invention relates to a method for evaluating a corroded part, the method evaluating a corroded part included in a metal member by using ultrasonic waves.

BACKGROUND ART

Conventionally, a method for specifying a corroded part included in a metal member by using ultrasonic waves has been well known. For example, in Patent Document 1, a configuration for evaluating a defect in a metallic cylindrical body by using an SH wave is disclosed. In Patent Document 2, a configuration for investigating a boundary portion between a pole and a road surface by using the SH wave or an SV wave is disclosed. Each of the methods is an evaluation method based on an echo of the corroded part.

CITATION LIST

Patent Literature

Patent Literature 1: JP-A-2004-361321
Patent Literature 2: JP-U-3198840

SUMMARY OF INVENTION

Problem to be Solved by the Invention

However, in a current situation, a waveform diagram of a received wave that is shown on a display unit includes noise, and a method for eliminating the noise has not been established. Thus, the waveform diagram in a state of including the noise is evaluated. For this reason, there is the limitation on improvement of evaluation accuracy, and proposal of a method capable of solving such a problem has been desired. For example, neither Patent Document 1 nor 2 discloses a method for handling such a problem.

Therefore, the present invention has a purpose of providing a method for evaluating a corroded part, the method capable of specifying only a waveform portion reflected by the corroded part in a waveform diagram of a received wave shown on a display unit and capable of evaluating the waveform portion.

Means for Solving Problem

The present invention is a method for evaluating a corroded part of a long metal member, one end portion of which is buried, by two probes using a transmission unit and a reception unit, the method comprising: transmitting an ultrasonic wave from the transmission unit that is arranged on an unburied surface on another end portion side of the metal member; making the ultrasonic wave pass through a stress concentrated part that is constrained from a portion therearound at the time of being buried and in which stress is more concentrated than the other portions; thereafter receiving the ultrasonic wave reflected by the corroded part by the reception unit that is arranged on the unburied surface on the other end portion side of the metal member; and showing a waveform diagram of the received wave in a specified echo display unit on the basis of a time axis and an intensity axis indicative of intensity of the received wave. A change in the waveform diagram of the received wave that is associated with a lapse of time is dynamically shown in the echo display unit while a separate distance between the corroded part and at least one of the transmission unit and the reception unit is changed. Only a waveform portion of the ultrasonic wave that is reflected by the corroded part is moved along the time axis in the waveform diagram of the received wave while the separate distance between the corroded part and the at least one of the transmission unit and the reception unit is changed. Only intensity of a noise waveform portion that is received by the reception unit is changed along the intensity axis in an intensity increase/reduction mode at a specified interval to show the change mode, and the waveform portion of the ultrasonic wave that is reflected by the corroded part is thereby separated from the noise waveform portion. In the echo display unit, the time axis is set as a horizontal axis, and the intensity axis is set as a vertical axis. The ultrasonic wave is a longitudinal-wave surface wave at 1 MHz or lower. The waveform diagram is a waveform diagram of an alternating wave of the unrectified received wave, the alternating wave having both of a positive wave portion and a negative wave portion.

Just as described, only the waveform portion of the ultrasonic wave that is reflected by the corroded part is moved along the time axis, and only the intensity of the noise waveform portion is changed in a manner to be increased/reduced along the intensity axis. In this way, it is possible to separate only the waveform portion of the ultrasonic wave reflected by the corroded part from the waveform diagram in which both of a waveform portion and a noise portion of an evaluation target are included, and it is thus possible to evaluate such a waveform portion in detail. For example, the waveform diagram of the received wave can be shown on an XY coordinates for observation of the waveform diagram. Since the ultrasonic wave is the longitudinal-wave surface wave at 1 MHz or lower, it is possible to reduce the noise generated by the constraint. Furthermore, the waveform diagram is a waveform diagram of an alternating wave of the unrectified received wave, and the alternating wave has both of a positive wave portion and a negative wave portion. Thus, there is an advantage that the change mode of the received wave can easily be checked.

The metal member is desirably a pole, a lower end portion of which is the one end portion and is buried in the ground.

Here, in general, stress is repeatedly applied to the pole in a specified direction due to swinging or the like. Thus, the stress concentrated part tends to be generated near the ground. For this reason, measurement by the above method is particularly useful.

Effects of Invention

In the method for evaluating the corroded part according to the present invention, it is possible to separate the noise portion of the received wave from the waveform portion of the ultrasonic wave reflected by the corroded part for discrimination. Therefore, it is possible to evaluate the corroded part with a high degree of accuracy.

DETAILED DESCRIPTION OF EMBODIMENTS

A description will be made on an example of a case where a method for evaluating a corroded part according to the present invention is applied to a metal pipe (a metal member) 60 in a long pole shape such as a signal pole, a traffic sign pole, or a lighting pole, a lower end portion of which is buried, with reference to the accompanying drawings. There is a case where front-rear/right-left directions and an up-down direction will be defined in the following description as a matter of convenience. However, this does not indicate that the present invention is used only in the directions described in the following description.

Figure 1:
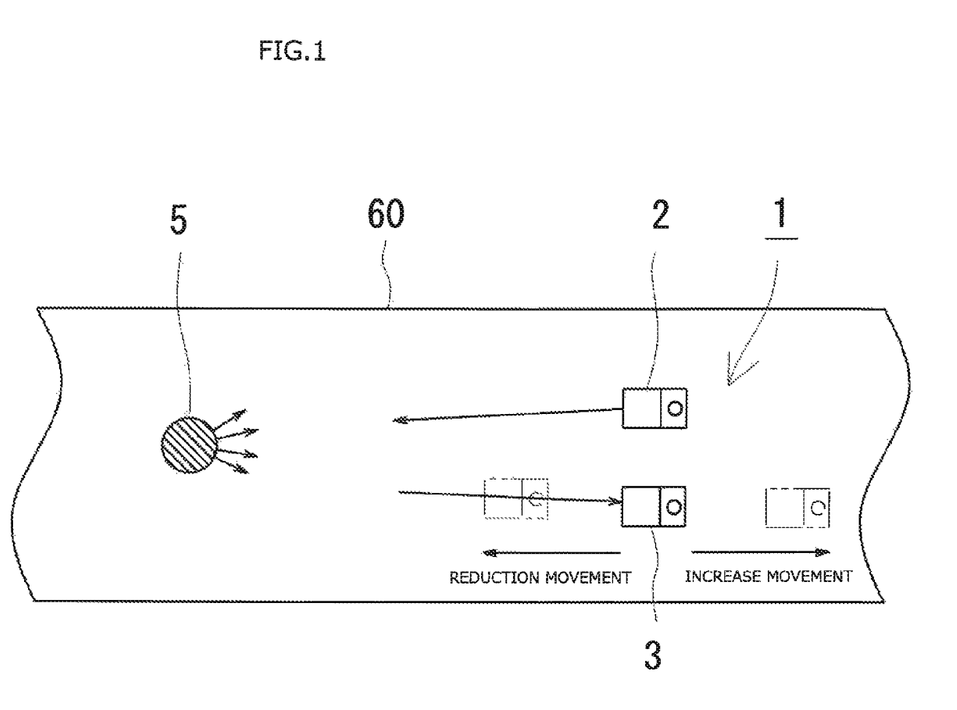
FIG. 1 is a view for illustrating an evaluation system.
Figure 2:
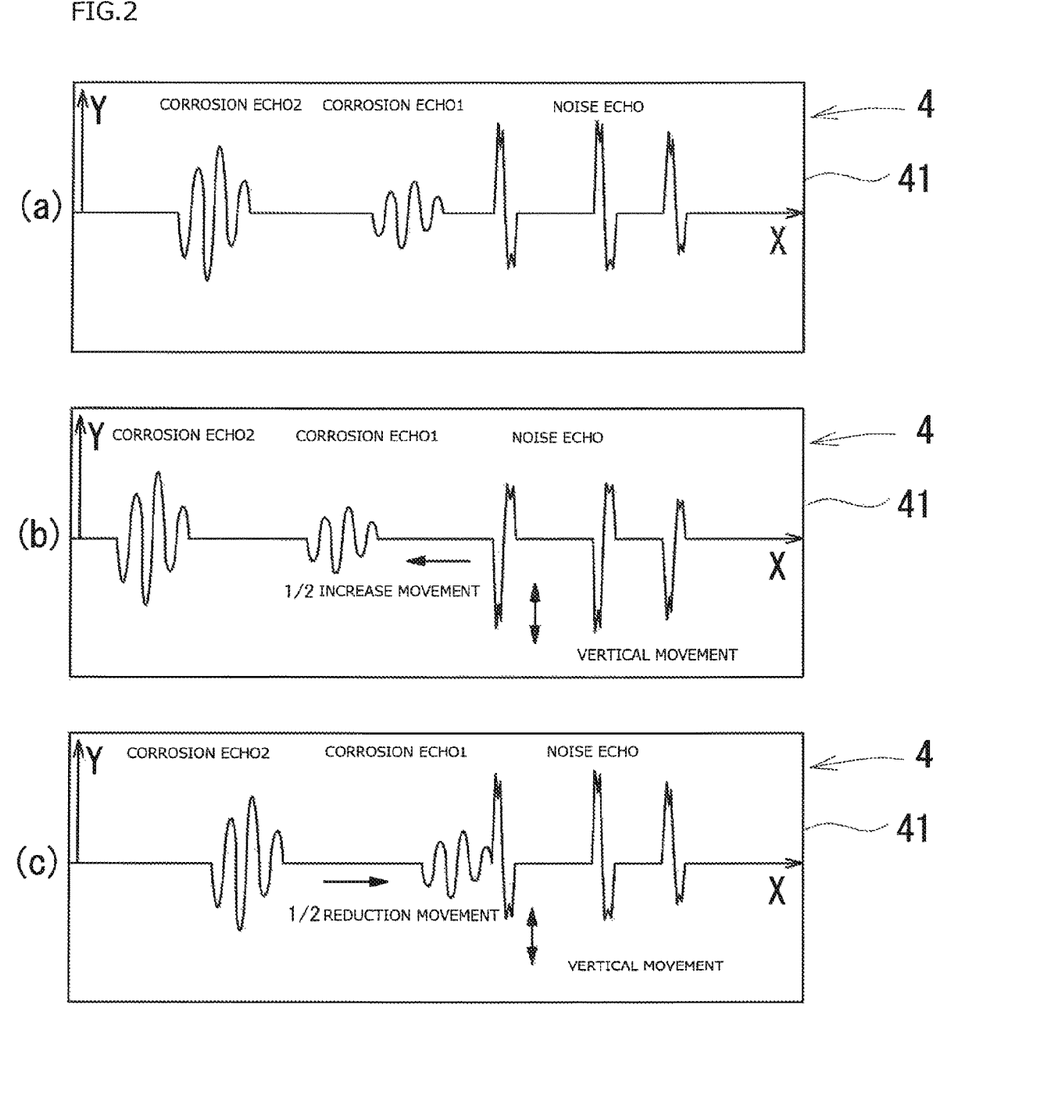
FIG. 2 includes diagrams for illustrating an echo display unit.

As illustrated in FIG. 1, an evaluation system 1 that is used to detect a corroded part 5 included in the metal pipe 60 includes: a transmission unit 2 that transmits a longitudinal-wave surface wave (ultrasonic wave) at 1 MHz or lower; a reception unit 3 as a sensor that receives the ultrasonic wave; and a waveform display device 4 that is equipped with an echo display unit 41 that shows a waveform diagram of the received wave and is illustrated in FIG. 2.

As illustrated in FIG. 2, in the echo display unit 41, an X-axis (horizontal axis) is set as a time axis, a Y-axis (vertical axis) is set as an intensity axis indicative of intensity of the received wave, and the waveform diagram of the received wave is shown two-dimensionally. The echo display unit 41 can show the received waveform diagram as a video, which allows a change in the waveform associated with a lapse of time to be comprehended dynamically.

Next, a detection procedure of the corroded part 5 included in the metal pipe 60 will be described.

First, the transmission unit 2 is arranged to a necessary portion on an unburied surface of the metal pipe 60, and the reception unit 3 is also arranged thereto. Then, the transmission unit 2 transmits the longitudinal-wave surface wave. The reception unit 3 receives the wave and identifies a location of the corroded part 5 of a buried portion by using a reflected wave. At this time, the waveform diagram of the received wave can be checked in the echo display unit 41 (see FIG. 2(a)).

Here, when the reception unit 3 is moved on the surface of the metal pipe 60 to change a separate distance between the corroded part 5 and the reception unit 3, as illustrated in FIGS. 2(b), (c) in the waveform diagram of the received wave, only a waveform portion A of the ultrasonic wave that is reflected by the corroded part 5 moves in the right-left direction along the X-axis. More specifically, as illustrated in FIG. 2(b), when the reception unit 3 is moved close to the corroded part 5, the waveform portion A moves in the left direction. Meanwhile, as illustrated in FIG. 2(c), when the reception unit 3 is moved away from the corroded part 5, the waveform portion A moves in the right direction.

In addition, when the reception unit 3 is moved on the surface of the metal pipe 60 to change the separate distance between the corroded part 5 and the reception unit 3, only intensity of a noise waveform portion B that is included in the received wave changes in the up-down direction along the Y-axis. More specifically, as illustrated in FIGS. 2(b), (c), when the reception unit 3 is moved close to or away from the corroded part 5, the intensity of the waveform portion B is increased/reduced at specified intervals.

Since only the waveform portion A of the ultrasonic wave, which is reflected by the corroded part 5, is moved along the X-axis, it is possible to separate the waveform portion A and the noise waveform portion B of the longitudinal-wave surface wave, which is reflected by the corroded part 5, from each other and then to evaluate the waveform portion A quantitatively.

Similarly, since only the intensity of the noise waveform portion B of the received wave, which is received by the reception unit 3, changes along the Y-axis, it is possible to separate the waveform portion A and the noise waveform portion B of the longitudinal-wave surface wave, which is reflected by the corroded part 5, from each other and then to evaluate the waveform portion A quantitatively.

The echo display unit 41 does not always have to have a video display function and only needs to have a function of allowing a change mode of the waveform diagram of the received wave, which is associated with the lapse of time, to be comprehended dynamically. However, the present invention differs from a method for evaluating the received wave by using the waveform diagram as a still image.

Instead of the reception unit 3, a position of the transmission unit 2 may be changed so as to change a separate distance between the transmission unit 2 and the corroded part 5. Alternatively, the separate distances may be changed by changing the positions of both of the transmission unit 2 and the reception unit 3.

Reasons for using the longitudinal wave are as follows. Firstly, due to a long wavelength, an output frequency of restricting noise is low. Secondly, a sound wave is the fastest. Thus, even when a mode conversion occurs by reflection or the like and the longitudinal wave is shifted to the horizontal wave, it is possible to identify the corroded part by looking at the fastest reflected wave. Thirdly, a change in an echo height is insignificant, and the echo height is stable. For example, there is an advantage that, even in the case where a pressing method at the time of pressing the sensor against a measurement surface varies, regardless of such variations, the change in the echo height is insignificant. Therefore, the echo height remains stable even when the sensor is moved. More specifically, in general, an error margin of the height is ±2 dB (approximately 1.3 to 0.8 time), and the echo can be observed while the sensor is moved.

As advantages of setting the above transmission frequency (1 MHz) range, firstly, the noise can be reduced, and secondly, a reflection range of the received wave is expanded due to a reduction in reflection directivity to widen a receivable range.

Advantages of using two of so-called probes as described above are as follows. Firstly, an impact of a transmission pulse is absent. Secondly, a position where the echo is reflected the most is not necessarily a transmission position, and a case with the unknown directivity can be handled. Thus a defect can be searched in multiple directions.

In the above embodiment, a measured pole transmission pulse is set as a reference of the echo height. As advantages thereof, firstly, an impact of a surface state is absent, secondly, an impact of a temperature change is absent due to the unchanged position, and thirdly, an impact of a curved surface is absent. Furthermore, the above configuration is most suited for sensitivity adjustment.

In the above configuration, the echo height of the ultrasonic wave is an evaluation target. Here, the height is defined as a ratio, and thus an evaluation such as "high" or "low" is desirably made with respect to a specified echo height (reference). In general, a so-called bottom surface echo, a reference defect (standard test piece), or the like is set as the reference. In this embodiment, it is often the case where the bottom surface echo does not appear. In addition, in the case of the reference defect, correction of the sensitivity possibly becomes extremely difficult due to the significant impact of the surface state, a temperature, or a curvature. For these reasons, the transmission wave is adopted. As a result, it is possible to solve disadvantages of the case with the reference defect by measuring the defect individually. In general, a surface of the corroded part 5 is uneven and expressed by the multiple reflected waves. Thus, the corroded part 5 can also be evaluated in consideration of an area thereof in addition to the echo height.

A detailed description will be made on usefulness of the present invention again.

Usually, of the received waves, a so-called corrosion echo tends to be low in the echo height while a noise echo tends to be high in the echo height. Thus, in the display unit, the corrosion echo tends to be brought into a state of being buried in the noise echo, which makes it difficult to discriminate the corrosion echo (For example, FIG. 5 in JP-U-3198840).

Here, a reason why the corrosion echo is generally small is because of an inconsistent shape of the corroded part. Thus, a reflection angle thereof varies with respect to an advancing direction of the ultrasonic wave. For example, there is a case where the echo disappears due to diffused reflection or the like of the ultrasonic wave. Thus, the intensity of the reflected wave that can be received by the reception unit is inevitably reduced. As a result, the intensity of the corrosion echo is reduced, and the identification of the corrosion echo becomes difficult.

Figure 3:
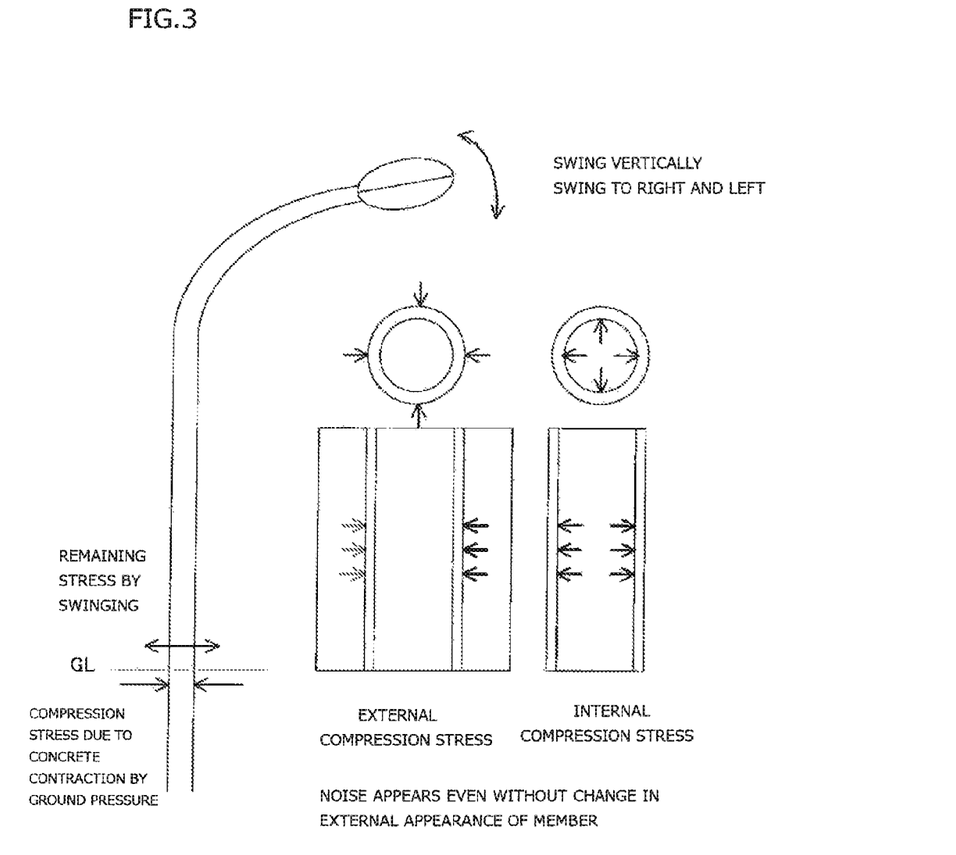
FIG. 3 is a view for illustrating a use state of a metal pipe.
Figure 4:
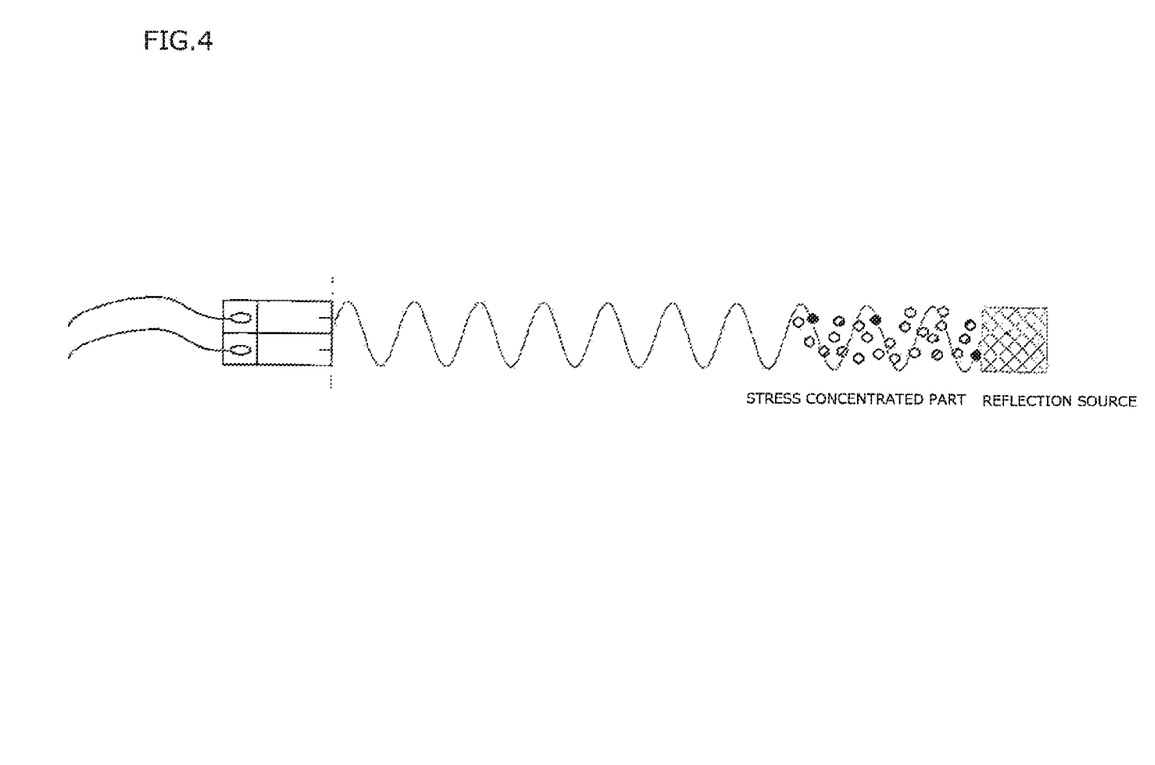
FIG. 4 is a conceptual view illustrating a stress concentrated part.

Meanwhile, in general, the echo height of the noise echo appears high especially when the pole, the lower end portion of which is buried, is the measurement target. A reason therefor is as follows. As illustrated in FIG. 3, a constraining portion (for example, a concrete floor or the like) is provided for the metal member as the pole. In a state where the metal member is fixed, stress is repeatedly applied to the constraining portion in a specified direction due to swinging of the pole or the like. For this reason, it is considered that such a metal material portion is more likely to be deformed than another portion and that crystal grains are coarsened. In this case, the ultrasonic wave that is transmitted from the transmission unit attached to a ground portion reaches a "stress concentrated part" that is the constraining portion near the ground before reaching the corroded part of the buried portion. Accordingly, when a distance of each of the parts is considered, as illustrated in FIG. 4, the ultrasonic wave reaches a large number of crystal grains (illustrated in hollow circles) in the "stress concentrated part", the distance of which is shorter than that of the corroded part before reaching the corroded part. As a result, a significantly larger echo than the corrosion echo is generated as noise at early timing (the crystal grains that the ultrasonic wave reaches are illustrated in black circles). In such principle, the corrosion echo tends to be buried in a noise echo group.

Just as described, in order to solve a problem that the waveform diagram, from which the corrosion echo is difficult to be discriminated, is shown, various methods have conventionally been implemented by reducing the echo height of the noise echo to be as low as possible and increasing the echo height of the corrosion echo to be as high as possible. For example, a method for finding a range where only the echo height of the corrosion echo is increased by changing a transmission frequency or a reception frequency has often been implemented. In addition, a method for showing the entire waveform of the received wave in order to completely comprehend the echo height of the corrosion echo for an analysis has been implemented frequently. When the received wave is rectified for the entire waveform, just as described, all positive and negative peaks of the received wave are aligned horizontally and thus can be visually checked at first glance.

However, in the above method, the entire waveform of the noise echo is also shown. In addition, as described above, since the noise tends to appear significantly, the complicated waveform diagram is still shown. As a result, a high skill is required for the analysis of the echo.

In view of the above, the present invention solves the problem of the related art and is useful in such a situation where the waveform diagram of the received wave, in which the maximum intensity of the waveform portion of the ultrasonic wave reflected by the corroded part is less than the maximum intensity of the noise waveform portion, is shown.

Figure 5:
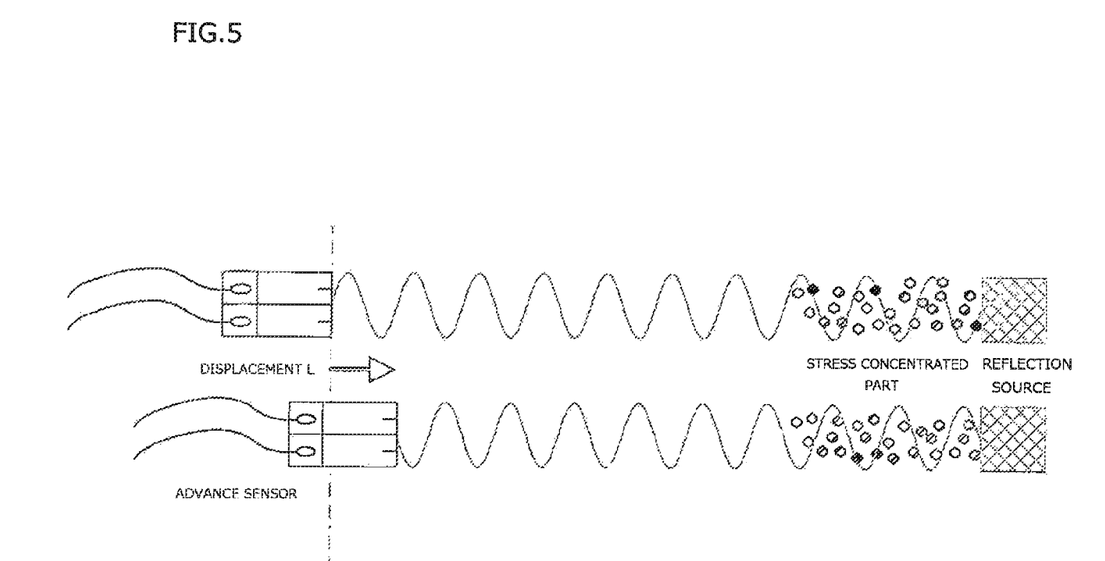
FIG. 5 is a conceptual view illustrating a change at the time when a transmission unit is moved.
Figure 6:
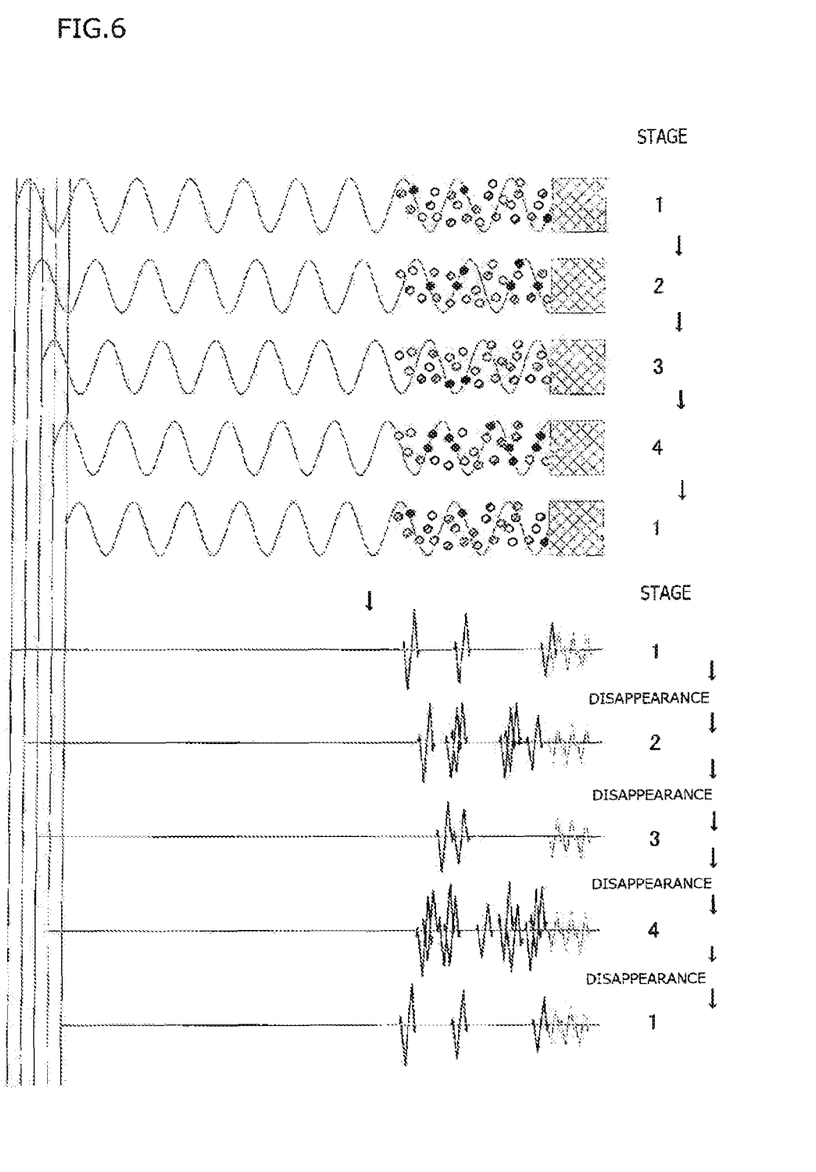
FIG. 6 is a view illustrating a change mode of a noise waveform portion.

In view of the above, as illustrated in FIG. 5, in the present invention, when the separate distance between the corroded part and at least one of the transmission unit and the reception unit is changed, an abutment position between the ultrasonic wave and each of the crystal grains in the "stress concentrated part" is changed from moment to moment in a process of movement of the sensor. For example, in FIG. 5, at an initial position, the echo in a state with the three abutment positions is detected (three black circles). When the position of the sensor is advanced from the initial position, a relative position between the ultrasonic wave and each of the crystal grains is changed, and the echo in a state with the two abutment positions between the ultrasonic wave and the crystal grain is detected (two black circles). In such a case, as illustrated in FIG. 6, the noise echo at the position where the transmitted ultrasonic wave abuts the crystal grain is detected at constant intervals. Thereafter, such a position is immediately changed, and the noise echo disappears suddenly. Soon thereafter, the noise echo suddenly appears at the abutment position against another crystal grain.

Furthermore, in the case where the sensor keeps being moved, the ultrasonic wave repeatedly abuts the crystal grains in the same mode. As a result, repeated abutment opportunities as described above occur at the intervals.

In the case where such a change mode (disappearance→appearance→disappearance→appearance) of the noise echo is observed in the dynamic display, it seems as if the intensity of the noise echo is increased and reduced with zero (the X-axis) being a center in cycles. Such a point that "only the intensity of the noise waveform portion is changed along the intensity axis in the intensity increase/reduction mode at the specified interval to show the change mode" is a part of constituent requirements of the present invention.

Figure 7:
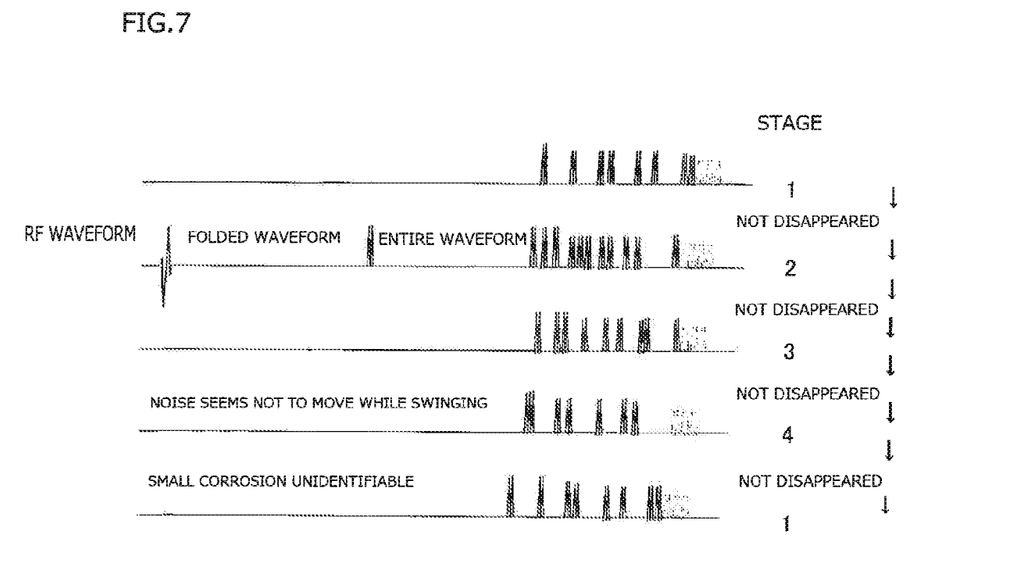
FIG. 7 is a view for illustrating a conventional example.

Furthermore, the present invention is characterized in that the ultrasonic wave is observed in a so-called RF waveform. The change mode of the noise echo, disappearance→appearance→disappearance→appearance, is observed in the form that upper ends and lower ends of the noise echo move vertically with zero (the X-axis) being the center. In the case where the noise echo and the corrosion echo are shown for the entire waveform, as illustrated in FIG. 7, a waveform is observed in a single wide "mountain" shape in a so-called "half" height in which positive wave portions and negative wave portions are aligned. As a result, it becomes difficult to observe the process of "disappearance" as described above. Thus, such a waveform is unsuited to observe the periodical increase/reduction change in the intensity of the noise echo.

The present invention has profound significance in intentionally selecting the low frequency at 1 MHz or lower. As it has been described so far, one of the important characteristics of the present invention is to show the periodical increase/reduction in the intensity of the noise echo. Thus, by adopting the low frequency in the range as described above, the number of waves per unit time is reduced, and a width of a so-called heave is increased. As a result, the number of abutment positions between the ultrasonic wave and the crystal grains is reduced as much as possible. In such a case, in the waveform diagram, the noise echo is shown in a mode of being scattered with a clearance being interposed in the horizontal axis (the time axis). Thus, the change mode of the noise echo shown in the RF waveform can further easily be observed. Meanwhile, in the case where a high frequency is adopted, the number of the abutment opportunity between the ultrasonic wave and the crystal grain is increased. As a result, such a problem occurs that the noise echo is shown in a concentrated manner and thus is complicated.

In addition, since the method using the two probes is adopted, extension of the transmission pulse is suppressed. Therefore, the noise can be reduced.

DESCRIPTION OF REFERENCE NUMERALS

2: Transmission unit
3: Reception unit
5: Corroded part
41: Echo display unit
60: Metal pipe (metal member)

What is claimed is:

1. A method for evaluating a corroded part of a long metal member, the long metal member having a first portion that is buried, a second portion that is an unburied portion, and a boundary portion between the first portion and the second portion, the boundary portion receiving stress more than any other portions of the long metal member, the first portion having the corroded part, the method comprising:
transmitting ultrasonic waves from a transmitter that is arranged on a surface of the second portion toward the corroded part in the first portion through the boundary portion;
receiving the ultrasonic waves reflected by any part of the long metal member by a receiver that is arranged on the surface of the second portion; and
showing a waveform diagram of the received ultrasonic waves on an echo display along a time axis and an intensity axis indicative of intensity of the received waves, the time axis being a horizontal axis, and the intensity axis being a vertical axis, wherein
the waveform diagram includes a first waveform corresponding to the ultrasonic waves reflected from the corroded part and a second waveform indicating noise components corresponding to the ultrasonic waves reflected from crystal grains in the boundary portion,
the method further comprises changing a distance between the corroded part and at least one of the transmitter and the receiver while transmitting the ultrasonic waves from the transmitter toward the corroded part,
the showing of the waveform diagram includes dynamically displaying temporal change in the waveform diagram as the distance changes,
the temporal change in the waveform diagram includes, with the distance changing, (1) moving only the first waveform along the time axis, and (2) increasing or decreasing only intensity of the second waveform that is the noise components from the boundary portion along the intensity axis at a predetermined period, separating the first waveform from the second waveform, the ultrasonic waves are a longitudinal-wave surface waves at 1 MHz or lower, and the waveform diagram is an RF waveform diagram of alternating waves of unrectified received waves, the alternating waves having both of positive wave portions and negative wave portions,
wherein the noise components of the second waveform in the RF waveform diagram includes a first noise component derived from a first crystal grain in the boundary portion and a second noise component derived from a second crystal grain in the boundary portion,
wherein the first noise component appears when the distance between the corroded part and at least one of the transmitter and the receiver is a first distance, and disappear when the distance is other than the first distance, and the second noise component appears when the distance between the corroded part and at least one of the transmitter and the receiver is a second distance, and disappear when the distance is other than the second distance, by which the first waveform is distinguished from the second waveform, and
wherein the first crystal grain is different from the second crystal grain, and the first distance is different from the second distance.

2. The method for evaluating the corroded part according to claim 1, wherein the long metal member is a pole, a lower end portion of which is the first portion and is buried in the ground.

* * * * *